United States Patent [19]

Eldin et al.

[11] 4,386,192

[45] May 31, 1983

[54] PROCESS FOR THE PREPARATION OF POLYMERS OF DEFINITE VISCOSITIES

[75] Inventors: Sameer H. Eldin, Birsfelden; Peter Grieshaber, Binningen, both of Switzerland

[73] Assignee: Ciba-Geigy Corporation, Ardsley, N.Y.

[21] Appl. No.: 347,401

[22] Filed: Feb. 10, 1982

[30] Foreign Application Priority Data

Feb. 19, 1981 [CH]  Switzerland .......................... 1108/81

[51] Int. Cl.³ .............................................. C08F 26/12
[52] U.S. Cl. ...................................... 526/218; 526/89; 526/263
[58] Field of Search ........................... 526/89, 263, 218

[56] References Cited

U.S. PATENT DOCUMENTS

| | | | |
|---|---|---|---|
| 3,721,654 | 3/1973 | Schlumbom et al. | 424/47 |
| 4,206,367 | 6/1980 | Eldin et al. | 548/309 |
| 4,256,867 | 3/1981 | Eldin et al. | 526/263 |

*Primary Examiner*—Harry Wong, Jr.
*Attorney, Agent, or Firm*—Luther A. R. Hall

[57] ABSTRACT

Process for the preparation of copolymers of definite specific viscosities from hydantoin vinyl ethers of the formula I and olefinically unsaturated compounds by free-radical polymerization of the monomers in a solvent mixture consisting of cyclohexane and toluene, it being possible to vary the specific viscosity of the copolymers within wide limits by altering the ratio of the two solvents. The meaning of the individual symbols can be seen in patent claim 1.

8 Claims, No Drawings

PROCESS FOR THE PREPARATION OF POLYMERS OF DEFINITE VISCOSITIES

The present invention relates to a process for the preparation of polymers having definite viscosities from hydantoin vinyl ethers and olefinically unsaturated monomers, using a solvent consisting of cyclohexane and toluene.

It is known that copolymers formed from hydantoin vinyl ethers and olefinically unsaturated compounds have a wide variety of possible uses. For example, it is apparent from U.S. Pat. Nos. 4,206,309 or its divisional U.S. Pat. No. 4,256,867 that these copolymers are suitable, inter alia, as thickeners, solubilisers, pseudoplasticisers or complexing agents. Polymers having definite molecular weights or specific viscosities are, however, necessary for these various applications. When regarded from the point of view of application, therefore, it is very important to be able to adjust the specific viscosity of polymers as desired over a wide range, since many central properties of the polymers, for example the complexing power or the thickening power, display, as is known, a marked dependence on the molecular weight or on the specific viscosity of the polymer. The said U.S. Pat. Nos. 4,206,309 or its divisional U.S. Pat. No. 4,256,867 does not provide any information on which process conditions must be varied in order to obtain copolymers of a desired specific viscosity.

Although U.S. Pat. No. 3,721,654, which has as its subject a process for the preparation of copolymers from maleic anhydride and 2-alkoxypropenes, discloses that copolymers having low viscosities are obtained if the maleic anhydride is employed in excess and that copolymers having high viscosities are obtained by employing the comonomers in equivalent quantities or using an excess of the 2-alkoxypropene, copolymers are obtained in unsatisfactory yields, in spite of relatively long polymerisation times.

It has now been found that copolymers of hydantoin vinyl ethers and maleic anhydride which have viscosities differing in a controlled manner over a wide range are obtained in equally high yields even if equimolar quantities of comonomers are used, if the copolymerisation is carried out in a solvent mixture consisting of cyclohexane and toluene, copolymers having low specific viscosities being obtained using small proportions of cyclohexane in the solvent mixture and copolymers having higher viscosities being obtained using higher proportions of cyclohexane.

The present invention therefore relates to a process for the preparation of copolymers having definite specific viscosities by copolymerising hydantoin vinyl ethers with copolymerisable compounds in an organic solvent and in the presence of a free-radical initiator, which comprises copolymerising, in the presence of an inert gas and within the temperature range from 20° to 110° C., (a) hydantoin vinyl ethers of the formula I

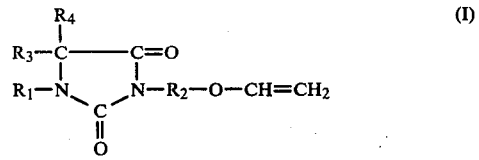

in which $R_1$ represents hydrogen or an organic radical, $R_2$ represents an alkylene having 1 to 6 C atoms or the radical $-(\text{alkylene}-O)_n$ alkylene in which the alkylenes contain 1 to 6 C atoms and n represents a number from 1 to 6, and $R_3$ and $R_4$ independently of one another each represent hydrogen, an alkyl having 1 to 6 C atoms, or an aryl or $R_3$ and $R_4$ together represent the tetramethylene or pentamethylene radical, with (b) olefinically unsaturated compounds, in a molar ratio of a:b equal to 1:0.01 up to 1:100, in a solvent mixture consisting of cyclohexane and toluene, the proportion of cyclohexane in the solvent mixture being 0.5 to 95% by volume and 0.1 to 30 g of the comonomers (a) and (b) being employed for 100 ml of the solvent mixture.

In the process according to the invention, it is preferable to use hydantoin vinyl ethers of the formula I in which $R_1$ represents hydrogen or methyl, $R_2$ represents ethylene, propylene or butylene and $R_3$ and $R_4$ independently of one another each represent hydrogen, methyl, ethyl or isopropyl or together represent the tetramethylene or pentamethylene radical; in particular, 3-vinyloxyethyl-5,5-dimethylhydantoin is employed.

The hydantoin vinyl ethers of the formula I are known compounds and can be prepared in accordance with the processes described in U.S. Pat. Nos. 4,206,309 or its divisional U.S. Pat. No. 4,256,867 by reacting hydantoins with ω-chloroalkyl vinyl ethers.

The olefinically unsaturated compounds (b) which are used are the monomers customary in free-radical polymerisation, such as vinyl acetate, acrylonitrile, vinyl ethers, diketene or derivatives of α,β-unsaturated monocarboxylic or dicarboxylic acids.

It is preferable to use as the monomer (b) the anhydrides of α,β-unsaturated dicarboxylic acids, such as maleic acid, chloromaleic acid, methylmaleic acid, ethylmaleic acid, dichloromaleic acid, diphenylmaleic acid, n-butylmaleic acid, phenylmaleic acid, chloromethylmaleic acid, bromophenylmaleic acid or itaconic acid; maleic anhydride is employed in particular.

When carrying out the process according to the invention in practice, the monomers and the solvent are initially taken and a clear solution is produced by warming. The free-radical initiator, dissolved in a little solvent is then added to this clear solution, after which the copolymerisation begins. In a preferred embodiment of the process according to the invention, the hydantoin vinyl ether of the formula I and the olefinically unsaturated compounds are employed in approximately equimolar quantities.

As mentioned initially, copolymers having low specific viscosities are obtained if the proportion of cyclohexane in the solvent mixture is low. It is preferable to use 0.5 to 85, in particular 0.5 to 80, % by volume of cyclohexane, relative to the total volume of the solvent mixture consisting of toluene and cyclohexane; copolymers having specific viscosities within the range from about 0.5 to 5.5 are then obtained.

The quantity of the comonomers in the solvent mixture can be varied within wide limits, but in general it should not exceed 30 g per 100 ml of solvent. It is preferable to employ 0.1 to 15 g, in particular between 5 and 10 g, of monomers per 100 ml of solvent.

The customary free-radical initiators can be used in the process according to the invention. Suitable initiators of this type are peroxides, for example potassium peroxysulfate or benzoyl peroxide, and also azo compounds, such as azoisobutyronitrile, or redox initiator systems, such as a mixture of iron(III) acetylacetonate, benzoin and benzoyl peroxide.

It is also possible to use the temperature conditions customary for free-radical polymerisation in the process. In general, the reaction is carried out between room temperature and 110° C., preferably between 50° and 110° C. and, in particular, within the temperature range from 50° to 75° C.

The copolymers which are obtained by the process according to the invention are characterised by their specific viscosity, which is a measure of the molecular weight of a polymer. The viscosity measurements are carried out using solutions of 1 g of copolymer in 100 ml of dimethylformamide (DMF).

As mentioned initially, the copolymers obtained by the process according to the invention can be used in many ways. Depending on their physical properties, they can be used as thickeners, solubilisers, crosslinking agents, flocculants, dispersants, adhesives, stiffening agents, binders, crystal growth regulators, pseudo-plasticisers (thixotropic agents), complexing agents and stabilising agents and also as builders for synthetic detergents, and are employed correspondingly in numerous branches of industry, for example in the paper industry as wet strength agents, in the textile industry as size, in the pharmaceutical and cosmetic industries and in the paint industry as thixotropic agents and in the agricultural chemicals industry as binders.

The following examples illustrate the process according to the invention in greater detail without limiting it.

EXAMPLE 1

Apparatus: a 350 ml flask equipped with a propeller stirrer, thermometer, condenser, heater and $N_2$ inlet.

| Substances: | | |
|---|---|---|
| 3-Vinyloxyethyl-5,5-dimethyl-hydantoin | 9.9 g | (0.05 mol) |
| Maleic anhydride (MA) | 4.9 g | (0.05 mol) |
| Azoisobutyronitrile | 0.074 g | (0.5% relative to monomers) |
| Cyclohexane and toluene, together | 200 ml | |
| (Monomers: solvent ratio = 7.4 g per 100 ml) | | |

The apparatus is flushed twice with $N_2$. A gentle stream of nitrogen is then maintained for the whole duration of the experiment. The vinyl ether, MA, 40 ml of cyclohexane and 155 ml of toluene are initially taken and a solution is produced by stirring. The mixture is heated to 60° C. The azoisobutyronitrile, dissolved in 5 ml of toluene, is added to the clear solution of the monomers. After a few minutes the solution becomes slightly cloudy and the polymerisation begins. After a polymerisation time of 6.4 hours altogether at 60±2° C., the mixture is cooled to room temperature and the product is filtered off under vacuum and dried to a constant weight in vacuo at 50° C.

Yield: 14.6 g=98.6% of theory.
Specific viscosity: 0.8250 (1% solution in DMF [dimethylformamide] at 25° C.)

EXAMPLES 2 TO 9

The following examples are carried out under the same conditions as in Example 1, but varying the cyclohexane:toluene ratio in the mixture. The results are shown in the following table:

TABLE

| | Solvent mixture | | | | | Specific viscosity (1% solution in DMF at 25° C.) |
|---|---|---|---|---|---|---|
| | Cyclohexane | | | Polymerisa- | Yield | |
| Examples | ml | % by volume | Toluene ml | tion time (hours) | % of theory | |
| 1 | 20 | 10 | 180 | 6.6 | 99.0 | 0.6242 |
| 3 | 1 | 0.5 | 199 | 6.3 | 99.3 | 0.5267 |
| 4 | 60 | 30 | 140 | 6.3 | 98.6 | 1.1815 |
| 5 | 80 | 40 | 120 | 6.5 | 98.6 | 1.6807 |
| 6 | 100 | 50 | 100 | 6.3 | 99.3 | 2.2013 |
| 7 | 120 | 60 | 80 | 6.3 | 98.6 | 2.9504 |
| 8 | 140 | 70 | 60 | 6.3 | 98.6 | 4.1642 |
| 9 | 160 | 80 | 40 | 6.3 | 98.6 | 5.2086 |

Examples 1–9 show how it is possible, with the aid of the process according to the invention, to vary the specific viscosity of the copolymers over a wide range without reducing the yields.

EXAMPLES 10 AND 11

When the following substances are used, the viscosities indicated in the table are achieved, using the apparatus described in Example 1 and applying the conditions indicated in the following table.

| Substances: | | |
|---|---|---|
| 3-Vinyloxyethyl-5-ethyl-5-methylhydantoin | 10.6 g | (0.05 mol) |
| Maleic anhydride | 4.9 g | (0.05 mol) |
| Azoisobutyronitrile | 0.0775 g | (0.05%, relative to monomers) |
| Cyclohexane and toluene, together | 200 ml | |
| (Monomers: solvent ratio = 7.8 g per 100 ml) | | |

| | Solvent mixture | | | | | Specific viscosity (1% solution in DMF at 25° C.) |
|---|---|---|---|---|---|---|
| | Cyclohexane | | | Polymerisa- | Yield | |
| Examples | ml | % by volume | Toluene ml | tion time (hours) | % of theory | |
| 10 | 1 | 0.5 | 199 | 5.9 | 98.7 | 0.4327 |
| 11 | 160 | 80 | 40 | 5.9 | 99.5 | 5.4733 |

EXAMPLES 12 AND 13

The process is carried out as described in Examples 10 and 11, but using 1-cyanoethyl-3-vinyloxyethyl-5,5-dimethylhydantoin as the hydantoin vinyl ether.

| Substances: | | |
|---|---|---|
| 1-Cyanoethyl-3-vinyloxyethyl-5,5-dimethylhydantoin | 12.6 g | (0.05 mol) |
| Maleic anhydride | 4.9 g | (0.05 mol) |
| Azoisobutyronitrile | 0.087 g | (0.5% relative to monomers) |
| Cyclohexane and toluene, together | 200 ml | |
| (Monomers: solvent ratio = 8.75 g per 100 ml) | | |

EXAMPLES 14 AND 15

The process is carried out as described in Examples 10 and 11, but using twice the quantity of monomers per 100 ml of solvent.

| Substances: | |
|---|---|
| 3-Vinyloxyethyl-5,5-dimethylhydantoin | 20.1 g |
| Maleic anhydride | 9.9 g |
| Azoisobutyronitrile | 0.15 g |
| Cyclohexane and toluene, together | 200 ml |
| (Monomers: solvent ratio = 15 g per 100 ml) | |

| | Solvent mixture | | Polymerisation time (hours) | Yield % of theory | Specific viscosity (1% solution in DMF at 25° C.) |
|---|---|---|---|---|---|
| | Cyclohexane | | | | |
| Examples | ml | % by volume | Toluene ml | | | |
| 12 | 1 | 0.5 | 199 | 5.9 | 98.8 | 0.3225 |
| 13 | 110 | 55 | 90 | 6 | 96.0 | 0.9136 |

| | Solvent mixture | | Polymerisation time (hours) | Yield % of theory | Specific viscosity (1% solution in DMF at 25° C.) |
|---|---|---|---|---|---|
| | Cyclohexane | | | | |
| Examples | ml | % by volume | Toluene ml | | | |
| 14 | 1 | 0.5 | 199 | 6 | 98 | 1.0956 |
| 15 | 140 | 80 | 60 | 5.9 | 96 | 16.7893 |

What is claimed is:

1. An improved process for preparing a copolymer and concomitantly controlling its specific viscosity to values between 0.3 and 16.8, as measured on a 1% solution in N,N-dimethylformamide at 25° C., by copolymerizing (a) a hydantoin vinyl ether of formula I

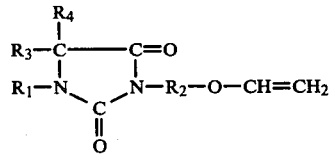

in which $R_1$ represents hydrogen or an organic radical, $R_2$ represents an alkylene having 1 to 6 C atoms or the radical $-(alkylene-O)_n$ alkylene in which the alkylenes contain 1 to 6 C atoms and n represents a number from 1 to 6, and $R_3$ and $R_4$ independently of one another each represent hydrogen, an alkyl having 1 to 6 C atoms, or an aryl or $R_3$ and $R_4$ together represent the tetramethylene or pentamethylene radical, with (b) an olefinically unsaturated polymerizable compound in a molar ratio of a:b of 1:0.01 to 1:100, in the presence of a free-radical initiator and of an inert gas at a temperature within the range of 20° C. to 110° C., wherein the improvement comprises
  carrying out the copolymerization reaction in a solvent mixture consisting of cyclohexane and toluene, the proportion of cyclohexane in the solvent mixture being 0.5 to 95% by volume, and where 0.1 to 30 grams of the comonomers (a) plus (b) are employed per each 100 ml of the solvent mixture.

2. A process according to claim 1, wherein a hydantoin vinyl ether of the formula I in which $R_1$ represents hydrogen or methyl, $R_2$ represents ethylene, propylene or butylene and $R_3$ and $R_4$ independently of one another each represent hydrogen, methyl, ethyl or isopropyl, or together represent the tetramethylene or pentamethylene radical, is used.

3. A process according to claim 1, wherein an $\alpha,\beta$-unsaturated dicarboxylic acid anhydride is employed as the olefinically unsaturated compound.

4. A process according to claim 1, wherein the hydantoin vinyl ether of the formula I and the olefinically unsaturated compound are employed in approximately equimolar quantities.

5. A process according to claim 1, wherein the proportion of cyclohexane in the solvent mixture is 0.5 to 85% by volume.

6. A process according to claim 1, wherein 0.1 to 15 g of comonomers are employed per each 100 ml of solvent mixture.

7. A process according to claim 1, wherein an azo compound is employed as the free-radical initiator.

8. A process according to claim 1, wherein the copolymerisation is carried out within the temperature range from 50° to 110° C.

* * * * *